United States Patent [19]

Bambara

[11] Patent Number: 4,843,885
[45] Date of Patent: Jul. 4, 1989

[54] ACOUSTIC DETECTION OF BEARING DEFECTS

[75] Inventor: Joseph E. Bambara, North Babylon, N.Y.

[73] Assignee: Servo Corporation of America, Hicksville, N.Y.

[21] Appl. No.: 168,975

[22] Filed: Mar. 16, 1988

Related U.S. Application Data

[63] Continuation-in-part of Ser. No. 104,801, Oct. 2, 1987, Pat. No. 4,790,190.

[51] Int. Cl.[4] ............................................. G01N 29/04
[52] U.S. Cl. .................................... 73/660; 246/169 S
[58] Field of Search ......................... 73/660, 659, 649; 246/169 S, 169 R, 169 A, 169 D, DIG. 1

[56] References Cited

U.S. PATENT DOCUMENTS 3,016,457  1/1962  Brown et al. .................... 246/169 S
3,558,876  1/1971  Tillman ............................ 246/169 S
4,129,276 12/1978  Svet ................................. 246/169 S
4,696,446  9/1987  Mochizuki et al. ............. 246/169 S Primary Examiner—Stewart J. Levy
Assistant Examiner—Louis M. Arana
Attorney, Agent, or Firm—Kane, Dalsimer, Sullivan, Kurucz, Levy, Eisele and Richard

[57] ABSTRACT

An apparatus for the detection of impact frequencies in moving railway train bearings which are characteristic of bearing defects. The apparatus transduces acoustic vibrations of the bearings into an electrical signal and extracts an envelope modulated carrier frequency component from the electric signal. The envelope is extracted from the carrier frequency component and is analyzed by a bandpass filter. The bandpass filter includes a switch capacitor filter controlled by a master clock which, in turn, is controlled by train speed and/or direction sensors positioned along the track on which the train travels.

8 Claims, 2 Drawing Sheets

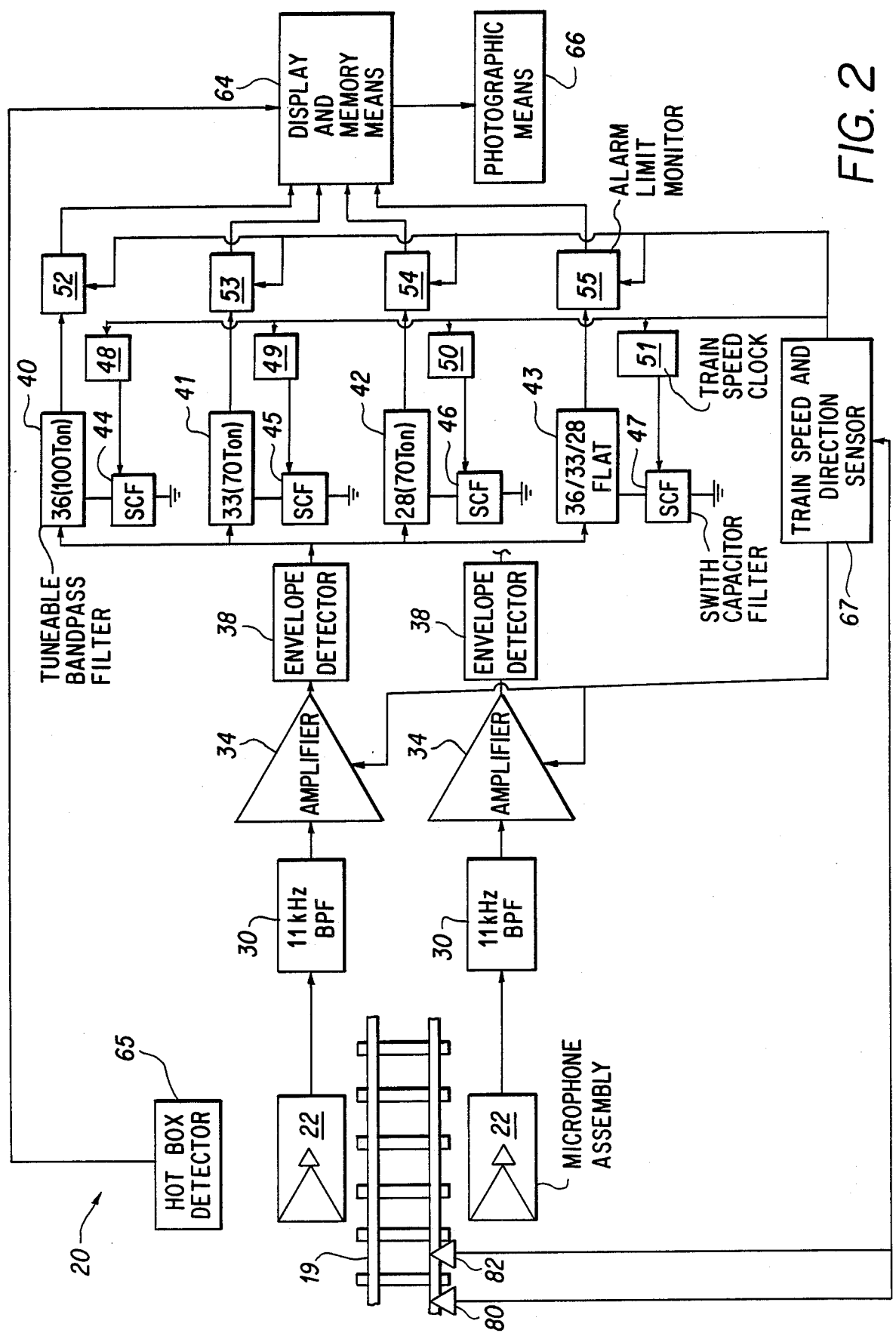

4,843,885

ACOUSTIC DETECTION OF BEARING DEFECTS

The present invention is a continuation-in-part of application Ser. No. 104,801 now U.S. Pat. No. 4,790,190 filed Oct. 2, 1987 for ON-LINE ACOUSTIC DETECTION OF BEARING DEFECTS.

BACKGROUND OF INVENTION

1. Field of Invention

The present invention relates to bearing defect detectors and in particular to an acoustic system for detecting defects in the bearings of moving railroad cars.

2. Description of the Prior Art

Heretofore, the detection of defects in railway car bearing has relied upon stationary infrared sensing means along railroad tracks to detect an abnormal heat rise associated with bearing failure in passing railroad cars. While such systems have enjoyed widespread use and an industry-wide reputation for reliability, they suffer from a serious drawback in that they detect a defect only after a damaging heat build-up has occurred within the bearing. Furthermore, this heat build-up often does not occur until a total bearing failure is imminent, thereby normally warranting an immediate stopping of the train so that an emergency field repair may be done. As this requires a delay in the train until a repair team may arrive with the necessary equipment, the total cost of this procedure can be very high.

It is known that defects in tapered roller bearings, such as those used in railroad cars, produce sounds, during operation, at characteristic frequencies dependent upon the location or type of defect (i.e., at the bearing cup, cone, or roller), the combination of the size of the wheel and the bearing capacity (frequently encountered combinations on railroads are a 28 inch wheel with a 70 ton capacity bearing, a 33 inch wheel with a 70 tone capacity bearing, and a 36 inch wheel with a 100 ton capacity bearing), and the speed of the train (which, of course, for a given diameter of the wheel, is proportional to the rotational frequency of the wheel). Additionally, irregularities in the wheel circumference ("flats") produce a characteristic frequency dependent upon rotational frequency of the wheel.

Thus, for any given train speed, a defective bearing will produce a sound at one of nine characteristic frequencies dependent upon the location of the defect and the combination of the train speed, wheel size and bearing capacity. Wheel flats will produce a sound at one of three additional characteristic frequencies. Ideally, one need need only listen for the sounds of a passing train to try to detect the characteristic sound frequencies to determine the condition of the bearings of the passing train. Unfortunately, railroad trains operate in extremely noisy environments. Train noises (such as wheel/rail rubbing, flange/rail squeal, loose equipment and cargo sounds, carbody noises, and clacking of rail joints for track circuits) and wind "swish" are low-frequency sounds which tend to camouflage the impact frequencies produced by a defective bearing. Thus, while the production of characteristic impact frequencies in a moving bearing have been known, it has heretofore been impossible to isolate the impact frequencies in a meaningful manner so as to provide useful and reliable information.

OBJECTS AND SUMMARY OF INVENTION

It is therefore an object of this invention to provide a means to detect a defective bearing, particularly in on-site railroad applications, before damaging heat build-up has occurred thereby giving repair crews sufficient early warning so as to allow the train to safely run to a place where repairs can be conveniently and inexpensively performed and/or to repair the bearing in its early stages of failure.

It is a further object of this invention to analyze, before repairs begin, the type of bearing defect (i.e., whether the defect is in the bearing cup, cone, or roller) which has occurred.

It is a further object of this invention to detect these defects reliably in a noisy environment such as is common in railroad and other industrial applications.

In analyzing the sounds generated by passing railroad trains, it has been noted that the impact frequencies characteristic of various bearing defects are generated in amplitude-modulated form on an acoustic carrier frequency band which is independent of the speed of the passing train. That is, while the bearing signature may be a function of train speed, the carrier frequency bands is not.

Therefore, apparatus which includes a microphone is placed beside railroad tracks so as to monitor the sounds emanating from the wheels and bearings of a passing railroad train. Preferably, microphones are placed adjacent opposite rails. A series of electronic amplifiers and preliminary filters is used to increase the output of the microphones to a usable voltage level and to filter extraneous frequencies from the resulting electronic signal. This allows the apparatus to operate effectively notwithstanding excessive ambient noise.

The gain of the amplifier is adjusted by the train speed and direction sensor so that the output of the amplifier is relatively constant in spite of significant volume changes due to train speed and direction (in that, under some circumstances, train direction is related to train loads, which is, in turn, related to the volume of noise generated thereby).

After electronic amplification and preliminary filtering, the signal consists predominantly of the preselected carrier frequency band which, in the presence of the characteristic impact frequencies of bearing defect, will be generated within an envelope of the characteristic impact frequencies. In other words, there is an amplitude-modulated signal with a preselected carrier frequency band within an envelope defined by any characteristic impact frequencies which may be present.

Standard amplitude demodulation techniques are used to extract the envelope in which the carrier frequency band is being transmitted. The extracted frequency signal is processed by a low-frequency bandpass filter which passes only the frequency range in which the various characteristic impact frequencies occur. The center frequency and the bandwidth of these filters are automatically increased with increasing train speed by the use of switch capacitors, responsive to a train speed and direction sensor.

A spectral analysis of the resulting signal is performed. The predominant frequency values of the spectral analysis are compared to the expected characteristic impact frequency values.

When a match between the predominant frequency values of the spectral analysis and the expected characteristic impact frequency value is found, the operators of the apparatus notify the operators of the train in order that appropriate plans for repair may be made.

BRIEF DESCRIPTION OF THE DRAWINGS

Further objects and advantages of the invention will become apparent from the following description and claims wherein:

FIG. 2 shows a schematic of the acoustic bearing defect detector apparatus of the present invention.

DETAILED DESCRIPTION OF THE PREFERRED EMBODIMENT

Figure 1:
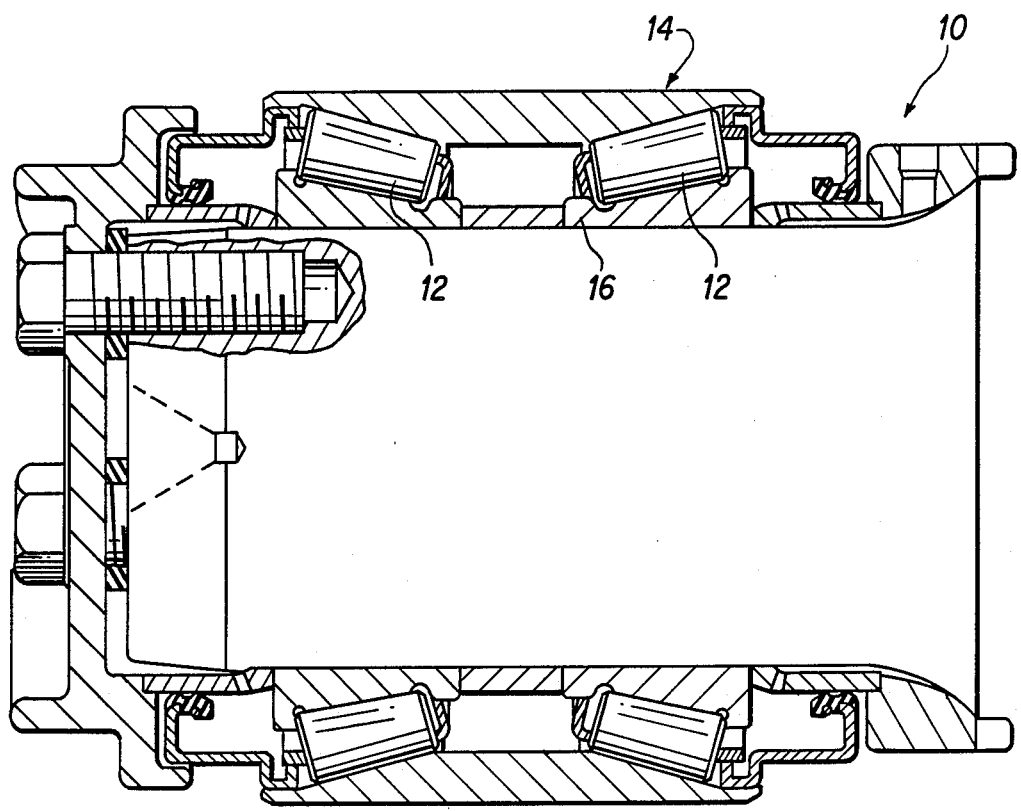
FIG. 1 shows a view in elevation of a typical tapered bearing as is used in railroad applications.

Referring now to the drawings in detail, FIG. 1 shows a tapered roller bearing assembly 10 such as those commonly used in railroad applications. Components which commonly fail are the surface of roller 12, the raceway of cup 14 and the raceway of cone 16. Upon failure of any component, a characteristic component-dependent rotational speed-dependent acoustic impact frequency generates a sound spectrum which amplitude modulates a carrier acoustic signal of rotational speed-independent frequency contained within said spectrum.

Referring now to FIG. 2 wherein the acoustical signal processor 20 is shown, input is received from a horn 22 wherein acoustic vibrations are transduced into an electrical signal. Ideally, this is a an electret microphone in a horn assembly with a cavity optimized for the desired bandpass of 10 to 12 kilohertz. A horn is desired as it provides the directional characteristics needed to isolate and identify defective bearing axle locations without ambiguity.

The Applicants, after extensive experimentation, have found that placement of the horn assembly is critical so as to avoid picking up excessive background noise (e.g., wheel/rail rubbing; flange/rail squeal; loose equipment or cargo rattling; car-body noise; clacking of rail joints for track circuits). Applicants have found that the horn must not be too far back so as to pick up excessive background noise but must be close enough so as to pick up a signature over a horizontal linear distance corresponding to one circumference or rotation of the wheel in order to capture defect repetition rate signatures that generally repeat once per wheel rotation. A wider range than this causes ambiguous results as the horn may monitor different axles simultaneously. A substantially lesser range than this may result in inadequate information for processing. However, a slightly less range than this was found advantageous in order to definitely isolate the axle of interest. Furthermore, the horn should not pick up a vertical distance above or below the wheel. Therefore, Applicants have found that a horn elongated in the horizontal plane and shortened in the vertical plane to collect over a wide horizontal angle so as to collect acoustic vibrations from a 60 degree horizontal angle (i.e. ±30 degrees from a line perpendicular to the rail) is well adapted to the present purpose. A preferable configuration is to place a horn on both sides of the tracks (one horn for each track). The horn should be placed four feet outboard of the rail gage 19 and collect sounds from a 60° horizontal angle, or somewhat over four feet of track. Additionally, the horn should point horizontally with its horizontal axis 12"-16" above the rail picking up sound vertically for about two feet.

A horn 22 is placed on both sides of the railroad track so as to monitor the bearings of wheels traversing both rail Additionally, each horn assembly 22 includes a test tone generator (not shown) which generates a test tone equal to a typical modulation carrier frequency (11.1 kHz) which is modulated sequentially to simulate a range of defects and possible train speeds. The test tone generator on one side of the track is used to generate test tones to calibrate the equipment on the other side of the track during idle periods.

A preamp is incorporated into the horn assembly to amplify the train noise and to prevent the broad range of background noise from overloading later amplifying and processing means. Additionally, a heater and protective shutter are added to the assembly to prevent ambient weather conditions from either damaging or altering the response of the microphone. The shutter opens as the train passes so as to not interfere with the acoustic analysis, but closes thereafter to protect the apparatus from the effects of weather or vandals. Additionally, the heater is turned off as the train passes to prevent the heater from generating alternating current frequency noise.

It will be understood that the circuity described hereafter is for a single horn 22. Both horns 22 have identical parallel circuitry.

The output of horn 22 is input into 11 kHz band pass filter 30. Amplifier 34 increases or decreases the electrical signal output from filter 30 to a usable level. There may be other amplifiers and/or buffers along the stream. The gain of one or more of the amplifiers is controlled by the train speed and direction indicator 67.

Envelope detector 38 acts as an amplitude demodulator for the output of the amplifier 34 by rejecting the preselected carrier frequency and passing the positive half of any envelope frequency which may be present.

The result of this amplitude demodulation, which may contain envelope frequencies which were modulating the preselected carrier frequencies, is processed by four parallel low-frequency tuneable bandpass filters 40-43 to remove any signal components which are spurious or not of interest, including any direct current component. The four filters correspond to one detector for each of these wheel sizes (28, 33 or 36 inch diameter, each detector being adapted as described later to detect roller, cup, and cone failures) and a fourth filter 43 to detect wheel flats in all sizes of wheels. To this end, the filters may readily be tuned as a function of train speed by utilizing switch capacitors 44-47. Such filters are characterized by output curves that follow the clock rate of a driving train speed clock 48-51. Thus, by setting the train speed clocks 48-51 as a function of the train speed to set the switch capacitors 44-47 of individual filters 40-43, the filter curves for each of the filters 40-43 remain optimized independently of the speed of the train. That is, the array of the filters 40-43 follow the actual train speed as determined by speed sensor 67. To this end, the center frequencies and bandwidths of the filters 40-43 are varied by changing the switch capacitor 44-47 values responsive to the train speed clocks 48-51 which are in turn responsive to train speed and direction sensor 67. Switch capacitors 44-47 are varied sufficiently rapidly so that filters 40-42 each detect three impact frequencies virtually simultaneously—those corresponding to roller, cup and cone defects. In a similar manner, the alarm limit monitors may also be controlled to follow the speed of the train by setting alarm limits based on train speed. The speed and direction sensor 67 may, for example, operate by determining the time required for a wheel of a passing train to activate a pair of wheel trips 80,82 positioned a fixed distance apart along a track rail. By also noting the sequence of activation of the wheel trips the direction of the train may also be readily determined.

The train speed is sued to vary the master clock rate hence tune the center frequency of filters 40-43. The train speed may be used to vary the gain of amplifier 34 since it has been found that more gain is required for slower train speed. The train direction may also be used to vary the gain of amplifier 34 depending upon whether a full or empty train is being observed as determined by the direction of travel of the train and it has been observed that an empty car requires greater gain. That is, an assumption is made that trains travelling in one direction (i.e. toward a mine) are empty and those travelling in the opposite direction (i.e. from the mine) are full.

The outputs of band-pass filters 40-43 are monitored by alarm limit monitors 52-55. The alarm limit monitors may be responsive to a number of threshold alarm level values of input amplitude, each corresponding to a different severity of the defect of interest. The threshold alarm level value may be adjusted in response to train speed sensor 67. Additionally, a prior art infrared detection means 65 may be used to detect heat build-up thereby verifying the severity of the bearing defect. As band-pass filters 40-43 have removed any direct current components of the signal, this monitoring must be done in the peak-to-D.C. mode. When an alarm limit monitor 52-55 sensing an input amplitude greater than a threshold value, the monitor 52-55 sends an appropriate message to display and memory means 64. Display and memory means 64 may be a display or light in a control room, it may include a central processing unit and memory means. Monitors 52-55 may also activate video or photographic means 66 to record the serial number of the passing. Train speed and direction sensor 67 may also include means for counting the number of railroad cars and/or axles (not shown) which pass, thereby providing means for determining which car and which side of the car has generated the impact frequencies characteristic of a bearing assembly defect. Preferably, records regarding the axle number side of the car with the bearing defect are generated using the nomenclature wherein axles are counted from the end of the train where the handbrake is (the "B" end).

Obviously, numerous modifications may be made to the apparatus without departing from the scope of the invention as defined in the appended claims.

What is claimed is:

1. In an apparatus for monitoring bearings of a railway train for defects during operation of the train along a section of track, said apparatus being of the type including train speed sensing means, means for transducing acoustic vibrations in said bearings into an electric signal, filter means for extracting an envelope modulated carrier frequency component from said electric signal, envelope detector means for extracting the envelope which modulates said carrier frequency component, and bandpass filter means for analyzing said envelope, the improvement wherein said bandpass filter includes switch capacitor filter means controlled by a master clock and said master clock is controlled by said train speed sensing means.

2. The apparatus in accordance with claim 1 further comprising an amplifier for adjusting the gain of said apparatus, said amplifier in turn being controlled by said train speed sensing means.

3. The apparatus in accordance with claim 1 further comprising load sensing means and an amplifier for adjusting the gain of said apparatus, said amplifier in turn being controlled by said load sensing means.

4. The apparatus in accordance with claim 1 wherein said bandpass filter means includes a plurality of filter elements operating in parallel, each of said elements includes switch capacitor filter means connected to the output of said master clock, thereby controlling frequency characteristics of said switch capacitor filter means.

5. The apparatus in accordance with claim 1 wherein said train speed sensing means includes a pair of spaced apart wheel sensors along said section of track and said master clock is further controlled by the sequence in which said wheel sensors are activated; and wherein said apparatus further comprises recording means to correlate alarm output from said bandpass filter means to a count of axles from said wheel sensors.

6. The apparatus in accordance with claim 5 for further comprising load sensing means.

7. The apparatus in accordance with claim 1 wherein said transducing means includes two microphone assemblies, one of said assemblies placed on each side of the section of track, substantially four feet away from the section of track, and optimized to detect sounds within substantially thirty degrees in both horizontal directions from a line perpendicular to the section of track.

8. The apparatus in accordance with claim 7 where both of said microphones assemblies include a tone generating means for simulating the passage of bearing with possible defects for calibration and testing of the other of said microphone assemblies.

* * * * *